United States Patent
Tatsumi (10) Patent No.: US 7,962,893 B2
(45) Date of Patent: Jun. 14, 2011

(54) SYSTEM AND PROGRAM FOR ASSISTING THE CREATION OF AUTOMATIC SAMPLER CONTROL PROGRAM

(75) Inventor: Nobuyuki Tatsumi, Kyoto (JP)

(73) Assignee: Shimadzu Corporation, Kyoto (JP)

(*) Notice: Subject to any disclaimer, the term of this patent is extended or adjusted under 35 U.S.C. 154(b) by 1007 days.

(21) Appl. No.: 11/775,508

(22) Filed: Jul. 10, 2007

(65) Prior Publication Data

US 2008/0052672 A1     Feb. 28, 2008

(30) Foreign Application Priority Data

Jul. 11, 2006   (JP) ................. 2006-190336

(51) Int. Cl.
    *G06F 9/44*     (2006.01)
(52) U.S. Cl. ...................... 717/106; 717/123
(58) Field of Classification Search .......... 717/106–115, 717/120, 123
    See application file for complete search history.

(56) References Cited

U.S. PATENT DOCUMENTS 6,344,172 B1 *   2/2002   Afeyan et al. ............... 422/70

FOREIGN PATENT DOCUMENTS

JP    2005-257575 A    9/2005

OTHER PUBLICATIONS

Keller et al, "A uniform proteomics MS/MS analysis platform utilizing open XML file formats", 2005, EMBO and Nature Publishing Group, pp. 1-8.*
Schafer et al., "Documenting Laboratory Workflows Using the Analytical Information Markup Language", 2004, The Association for Laboratory Automation, pp. 375-381.*

* cited by examiner

*Primary Examiner* — Ted T Vo
(74) *Attorney, Agent, or Firm* — Westerman, Hattori, Daniels & Adrian, LLP

(57) ABSTRACT

In conventional cases, a control program for an automatic sampler for a liquid chromatograph has to be created by combining operational commands. To do this, users have to know the meaning of each command and learn the programming method. Therefore, the conventional method is difficult for those who are not skilled in programming. In contrast, with the system for assisting the creation of an automatic sampler control program, the user can create the control program by selecting instructional sentences written in a natural language. The system uses a definition file in which each instructional sentence is associated with one or more operational commands. When the user selects one of instructional sentences displayed on a display screen, the system includes one or more operational commands corresponding to the selected instructional sentence into the control program. By selecting one instructional sentence after another over multiple sentence input lines, the user can easily create a control program consisting of a sequence of operational commands.

5 Claims, 6 Drawing Sheets

Fig. 7

| No | Operation |
|---|---|
| 1 | Rinse the injection port with cleaning fluid 1 |
| | |

| No | Command | Parameter | Comment |
|---|---|---|---|
| 1 | AO= | 13 | Rinse the injection port with cleaning fluid 1 |
| 2 | IRINSE | RV,RS | |

Help: Set parameters for IRINSE: RV=volume of cleaning fluid, RS=flow rate while rinsing

Fig. 8

| No | Operation |
|---|---|
| 1 | Rinse the injection port with cleaning fluid 1 |
| 2 | Rinse the injection port with mobile phase |
| 3 | Inject the sample |
| 4 | Set the operation waiting time |
| 5 | Switch the high-pressure valve to the load side for rotary-washing |
| 6 | Rinse the injection port with cleaning fluid 2 |
| 7 | Rotary-wash the high-pressure valve |
| 8 | Rinse the injection port with mobile phase |
| 9 | End |

| No | Command | Parameter | Comment |
|---|---|---|---|
| 1 | AO= | 13 | Rinse the injection port with cleaning fluid 1 |
| 2 | IRINSE | RV,RS | |
| 3 | AO= | 15 | Rinse the injection port with mobile phase |
| 4 | IRINSE | RV,RS | |
| 5 | VIAL | SN | Inject the sample |
| 6 | NSTRK | NS | |
| 7 | ASPIR | IV,SS | |
| 8 | INJP | | |
| 9 | SINJ | | |
| 10 | WAIT | 1 | Set the operation waiting time |
| 11 | VLOAD | | Switch the high-pressure valve to the load side |
| 12 | AO= | 14 | |
| 13 | IRINSE | RV,RS | |
| 14 | VINJ | | Rotary-wash the high-pressure valve |
| 15 | VLOAD | | |
| 16 | AO= | 15 | Rinse the injection port with mobile phase |
| 17 | IRINSE | RV,RS | |
| 18 | END | | |

Help: Set parameters for IRINSE: RV=volume of cleaning fluid, RS=flow rate while rinsing

Fig. 9

```
<?xml version="1.0">
<type>
        SIL-20A
</type>
<config>
        <menu data>
                <menu line>1</menu line>
                <menu list>Rinsing</menu list>
        </menu data>
        <menu data>
                <menu line>2</menu line>
                <menu list>Reaction</menu list>
        </menu data>
        <menu data>
                <menu line>3</menu line>
                <menu list>Advanced</menu list>
        </menu data>
</config>
<pret list>
        <prog set>
                <help>
                        Set parameters for IRINSE: RV=volume of cleaning fluid,
                        RS=flow rate while rinsing
                </help>
                <display position>
                        1
                </display position>
                <operation>
                        Rinse the injection port with cleaning fluid 1
                </operation>
                <prog list>
                        <command>
                                AO=
                        </command>
                        <parameter>
                                13
                        </parameter>
                        <command>
                                IRINSE
                        </command>
                        <parameter>
                                RV,RS
                        </parameter>
                </prog list>
        </prog set>
        <prog set>
                <help>
                        . . . .
</pret list>
```

Fig. 10

File (F) Edit (E) Output (V) Help (H)

Help | Set parameters for IRINSE: RV=volume of cleaning fluid, RS=flow rate while rinsing

[Output as XML] [Output as Text] [Output as Text with Comments] [Reset]

| No | Operation |
|---|---|
| 1 | Rinse the injection port with cleaning fluid 1 |
| 2 | Rinse the injection port with mobile phase |
| 3 | Inject the sample |
| 4 | Set the operation waiting time |
| 5 | Switch the high-pressure valve to the load side for rotary-washing |
| 6 | Rinse the injection port with cleaning fluid 2 |
| 7 | Rotary-wash the high-pressure valve |
| 8 | Rinse the injection port with mobile phase |
| 9 | End |

| No | Command | Parameter | Comment |
|---|---|---|---|
| 1 | AO= | 13 | Rinse the injection port with cleaning fluid 1 |
| 2 | IRINSE | RV,RS | |
| 3 | AO= | 15 | Rinse the injection port with mobile phase |
| 4 | IRINSE | RV,RS | |
| 5 | VIAL | SN | Inject the sample |
| ... | | | |
| 13 | IRINSE | RV,R | |
| 14 | VINJ | | |
| 15 | VLOAD | | |
| 16 | AO= | 15 | Rinse the injection port with mobile phase |
| 17 | IRINSE | RV,RS | |
| 18 | END | | |

Submenus: Rinsing → Rinse the injection port with cleaning fluid 1; Reaction → Rinse the injection port with cleaning fluid 2; Advanced → Rinse the sample port with cleaning fluid 1; Rinse the sample port with cleaning fluid 2

Fig. 11

PRET PROGRAM                         FILE 1

| # | COMMAND | VALUE | BYTES LEFT 250 |
|---|---|---|---|
| 0 | | | |

```
0 INJ. P      6 EVENT     12 RINSE    17 DILUTE
1 HOME        7 N. STRK   13 IRINSE   18 MIX
2 V. INJ      8 WAIT      14 ASPIR    19 IF
3 V. LORD     9 VIAL      15 DISP     20 FOR
4 S. INJ     10 GOTO      16 AIR. A   21 NEXT
5 CALL       11 NEEDLE
```

SAMPLE NUMBER (から) 0-99 101 102 103

FILE    PRINT    EDIT    EXIT    READY

SYSTEM AND PROGRAM FOR ASSISTING THE CREATION OF AUTOMATIC SAMPLER CONTROL PROGRAM

The present invention relates to an automatic sampler for automatically introducing one or more samples into an analyzing apparatus, such as a liquid chromatograph. Particularly, it relates to a system and program for assisting the creation of a program for controlling an automatic sampler.

BACKGROUND OF THE INVENTION

In an analysis using a liquid chromatograph, an automatic sampler is used to automatically introduce multiple samples into a column in a predetermined order (for example, refer to Japanese Unexamined Patent Application Publication No. 2005-257575).

Figure 11:
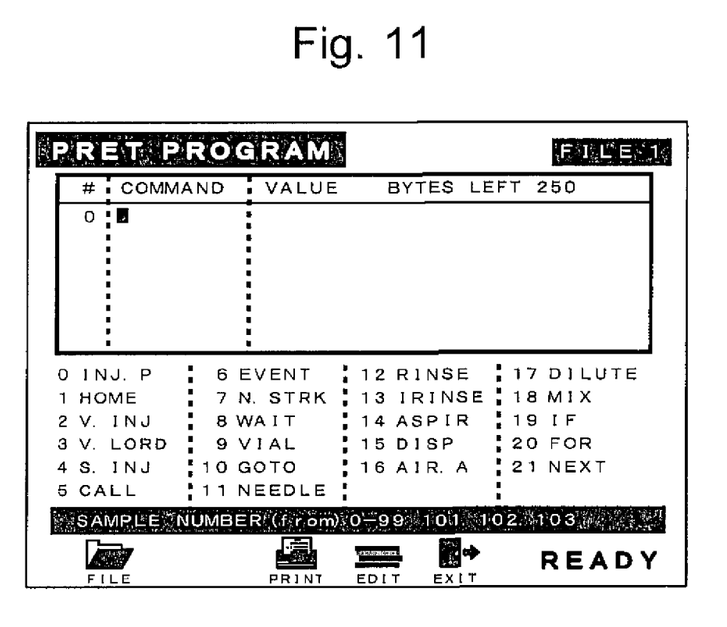
FIG. 11 shows a program edition screen of a conventional program for assisting the creation of an automatic sampler control program.

To carry out an analysis using an automatic sampler, the user responsible for that analysis has to customize its operation according to his or her intention. For that purpose, the user needs to create a control program consisting of an appropriately organized sequence of commands for giving instructions to the automatic sampler. FIG. 11 shows a program edition screen of a conventional program for creating an automatic sampler control program. On this screen, the user can create a command sequence by selecting one command after another from the list of operational commands numbering from 0 to 21. In this example, some commands are intended to actually control the operation of the device, while others are merely used for conditional processing and branching, such as "IF" or "GOTO." The parameter required by each command needs to be manually entered.

In creating a control program by selecting operational commands as previously described, to make the automatic sampler operate in the intended manner, the user has to (1) learn the meaning of each command, (2) understand the procedure for creating a program, and (3) know the flow-path structure of the automatic sampler to determine an appropriate operational sequence. Moreover, it is necessary to know the meaning of each parameter used for each command.

Suppose that the user wants to "inject samples." To make the automatic sampler perform this complete, independent operation, he or she has to select five operational commands ("VIAL", "NSTRK", "ASPIR", "INJP" and "SINJ") one after another and combine them in the correct order. Users who do not know this combination and order must refer to a manual or consult someone who is familiar with the device.

If the user wants to include conditional processing and branching in the sequence, it is necessary to use such commands in compliance with the description rules specific to the assistant program he or she is using.

Thus, the conventional method for performing an analysis with an automatic sampler requires users to learn many things in addition to the analysis technique. Therefore, some users, particularly those who are not skilled in computer programming, often feel this method is considerably difficult to learn and use. What is more, selecting and putting one command after another is inherently time and labor consuming.

After various efforts to solve such problems, the present inventor has conceived the idea of a system with which the user can create a control program by selecting a natural language phrase (or a sentence) each corresponding to a complete, independent operation of the automatic sampler. The new system differs from the conventional one where the user has to select operational commands one after another to create a control program.

SUMMARY OF THE INVENTION

Thus, the present invention provides a system for assisting the creation of an automatic sampler control program including a sequence of operational commands, wherein:

the system has access to a definition file in which a plurality of instructional sentences are written in a natural language and each instructional sentence is associated with one or more operational commands corresponding to that instructional sentence, and the system further includes:

an input assistant for selecting one of the sentence input lines in each of which an instructional sentence can be written, for selecting an instructional sentence, for inputting a parameter, and for entering an output command;

a candidate selection assistant acting in response to a selection of one sentence input line, to read a plurality of instructional sentences from the definition file and display the read-out instructional sentences as candidates;

a program creator acting in response to a selection of one of the instructional sentences displayed as the candidates, to create the control program by reading one or more operational commands corresponding to the selected instructional sentence from the definition file and then writing the read-out operational commands in the control program in accordance with the order of the instructional sentences written in the sentence input lines;

a parameter-setting assistant acting in response to an input of a parameter of one operational command included in the control program, to associate the inputted parameter with the aforementioned one operational command; and an outputter acting in response to the output command, to output the control program in a predetermined file format.

In conventional cases, users who were not familiar with the meanings of the commands and the operations of the program could not create a control program for an automatic sampler. In contrast, with the system for assisting the creation of an automatic sampler control program, the user can create an automatic sampler control program by simply selecting one or more instructional sentences described in a natural language and displayed on a screen as candidates. Even an analyst who does not know the meaning of each operational command or who does not sufficiently have necessary knowledge for creating the control program can create an automatic sampler control program easily.

In the definition file, each instructional sentence is typically associated with multiple operational commands. The user has only to select one of the instructional sentences displayed as the candidates, using a mouse or other input devices. Then, multiple commands corresponding to the selected instructional sentence are automatically written in the control program. Thus, the troublesome operation of selecting multiple commands one after another is eliminated. As a result, the control program can be rapidly created with a lower probability of programming errors.

In a preferable mode of the system of the present invention:

the definition file contains candidate information organized in a hierarchical structure having multiple levels, with the aforementioned instructional sentences located at the lowest level; and the candidate selection assistant hierarchically displays the candidates on the basis of the candidate information.

In this mode of the invention, the number of choices displayed on the screen by the candidate selection assistant at one time is reduced, so that the information is easier to discern by sight. The user can reach his or her objective instructional sentence by narrowing down the choices from higher to lower levels. This stepwise narrowing process, by which the user can be correctly guided to the desired control operation, effectively improves the user-friendliness of the system, particularly when there are a large number of candidate instructional sentences, or when there are many kinds of control operations.

In another preferable mode of the system of the present invention:
the definition file specifies an initial value of each parameter of one or more specific operational commands; and
for each operational command used in the control program to be created, if the initial value of each parameter of that operational command is defined, the program creator writes the operational command with the initial value of each parameter in the control program.

In this mode of the invention, the initial value of each parameter can be displayed on the screen to help the user set or change the parameter.

EXPLANATION OF THE NUMERALS

10 . . . Central Processing Unit (CPU)
12 . . . Memory
14 . . . Display Unit
16 . . . Input Unit
20 . . . Storage Unit
21 . . . Program for Assisting the Creation of Automatic Sampler Control Program
22 . . . Definition File
23 . . . Operating System (OS)

DETAILED DESCRIPTION OF A PREFERRED EMBODIMENT

Figure 1:
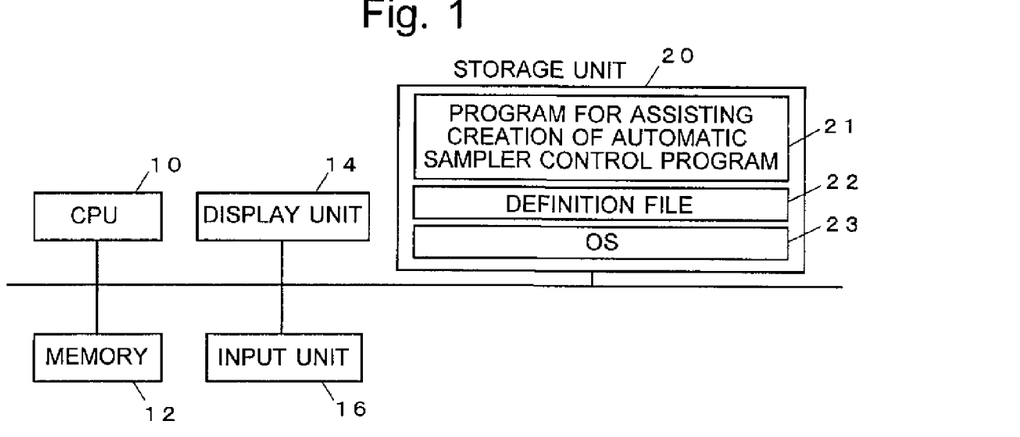
FIG. 1 shows an example of the hardware construction of the system according to the present invention.

FIG. 1 shows the hardware construction of a system for assisting the creation of an automatic sampler control program according to an embodiment of the present invention. This system includes a central processing unit (CPU) 10 to which various devices are connected, such as a memory 12, a display unit 14, an input unit 16 including a mouse, keyboard or similar device, and a storage unit 20 such as a hard disk drive. In the storage unit 20, a program 21 for assisting the creation of an automatic sampler control program (the program 21 is called the assisting program 21 hereinafter), a definition file 22 and an operation system (OS) 23 are stored.

Figure 2:
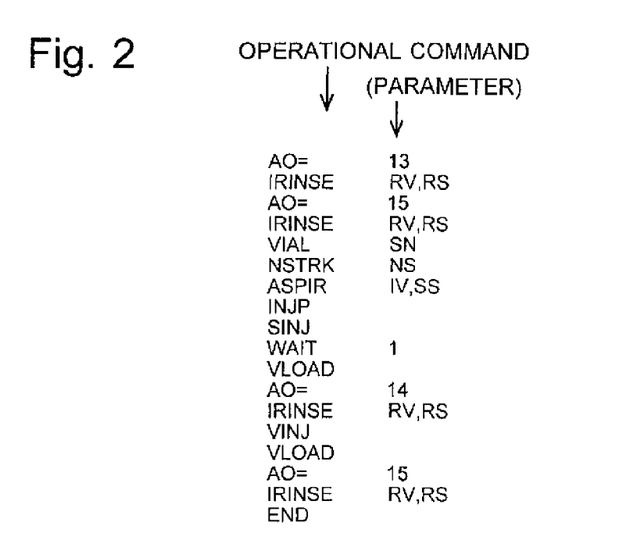
FIG. 2 shows an example of the automatic sampler control program.

In the present invention, the "automatic sampler control program", which may be simply called the "control program" in this specification, is composed of a plurality of sequentially arranged operational commands for controlling the automatic sampler. FIG. 2 shows an example of the control program. Some operational commands require a parameter setting, while others do not.

The control program created by the system of the present invention is the same as that created by a conventional, command-based system, such as the one shown in FIG. 11.

Figure 3:
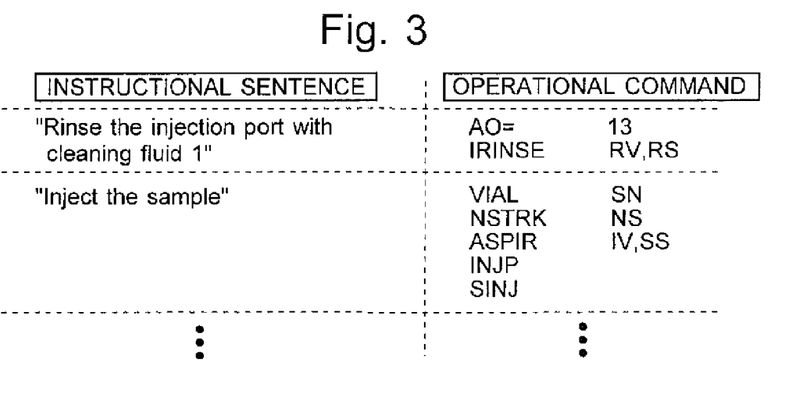
FIG. 3 conceptually shows the structure of the definition file.

FIG. 3 conceptually shows the structure of the definition file 22. The definition file 22 has all the possible instructional sentences written in it, with each instructional sentence associated with one or more corresponding operational commands, as will be detailed later. From this definition file 22, the CPU 10 can obtain instructional sentences to be presented on the display unit 14 and one or more operational commands corresponding to each instructional sentence.

The "instructional sentence" in the present invention is a natural language sentence that describes a complete, independent instruction. For example, "Rinse the injection port with the cleaning fluid 1", "Inject the sample" and "Set the operation waiting time" are complete, independent instructions. Each instructional sentence is associated with one or more operational commands, which are appropriately ordered so that the automatic sampler is controlled as intended by the instruction sentence concerned. The definition file 22 also includes instructional sentences for carrying out conditional processing and branching.

It should be noted that the instructional sentences can be written in any natural language as long as the language is understandable to those skilled in the art of the invention even without any special knowledge of computer programming.

Details of the definition file 22 are as follows:
In FIG. 3, the instructional sentence "Rinse the injection port with the cleaning fluid 1" is associated with two operational commands "AO=" and "IRINSE" written in this order in two lines. The first command "AO=" has a parameter with an initial value of "13." Similarly, the second command "IRINSE" has its parameter initialized to "RV, RS."

Another instructional sentence "Inject a sample" is associated with five operational commands "VIAL", "NSTRK", "ASPIR", "INJP" and "SINJ" written in this order. Of these commands, "VIAL", "NSTRK" and "ASPIR" have parameters with initial values of "SN", "NS" and "IV, SS", respectively. No parameter value is given to the commands "INJP" and "SINJ" because they inherently require no parameter setting.

The definition file 22 can be created in any file format, including the CSV (comma spaced values), TSV (tab spaced values) and XML (extensible markup language) formats. It is preferable to use a file format that allows users to freely edit the definition data using a text editor or similar software application.

Figure 4:
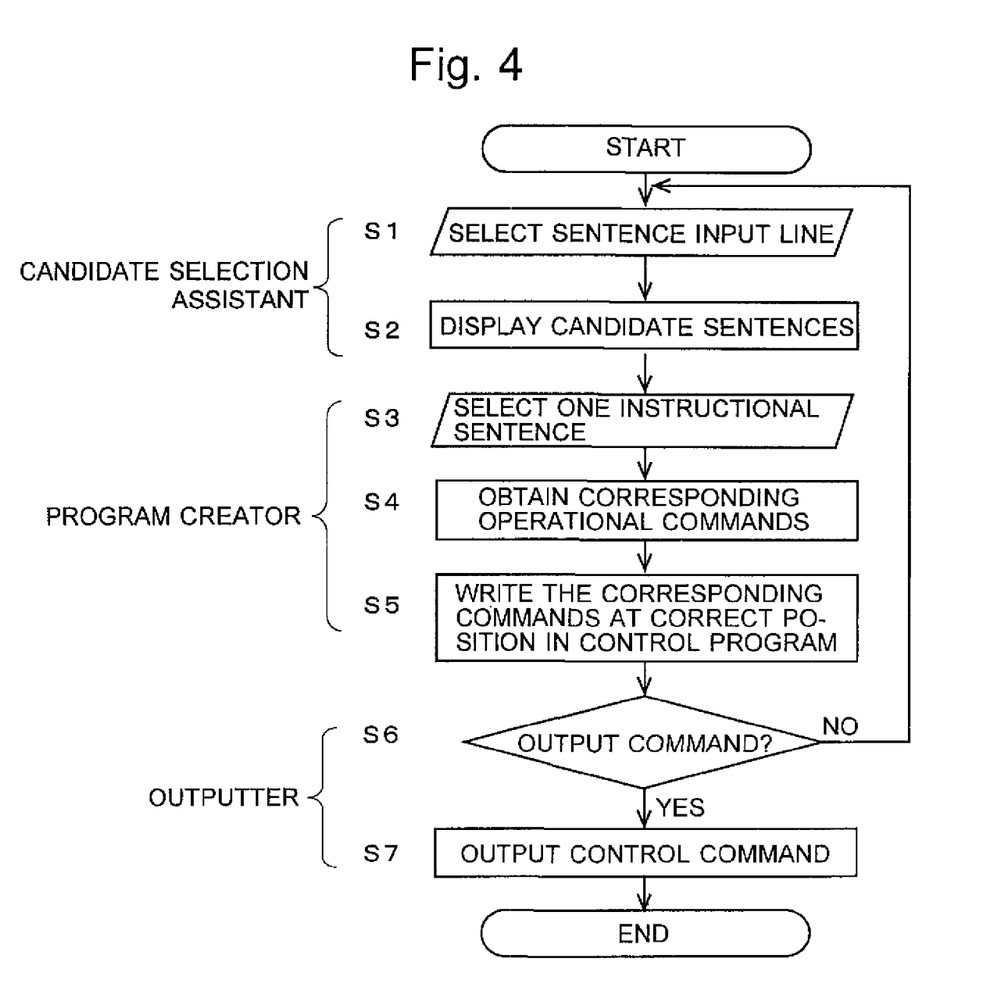
FIG. 4 shows the flowchart of the operation of a program for assisting the creation of an automatic sampler control program according to the present invention.
Figure 5:
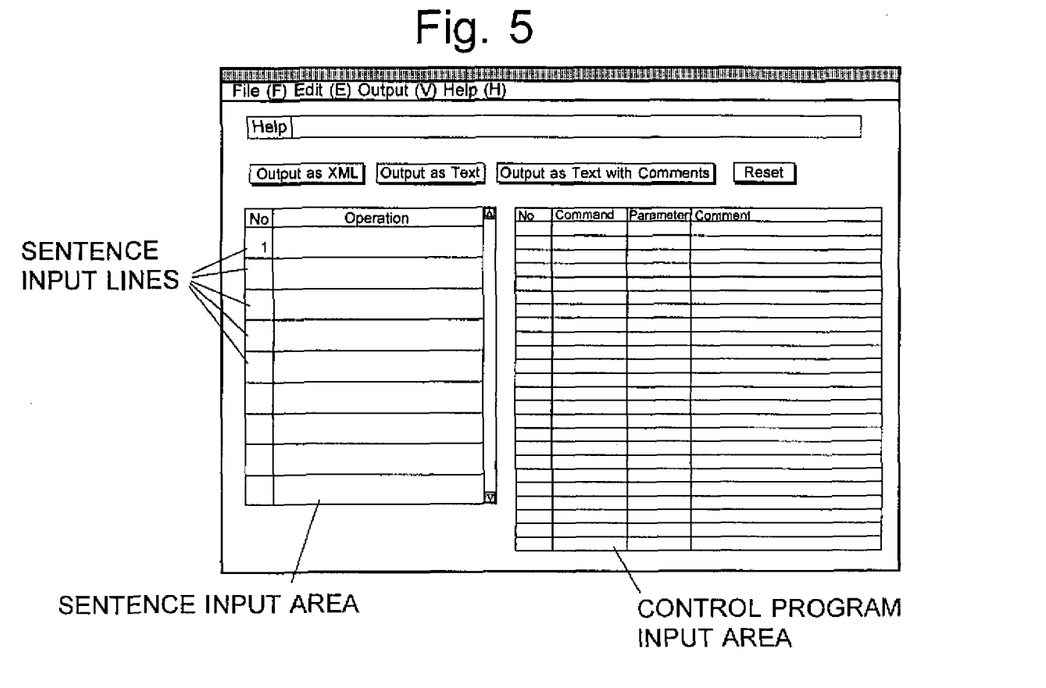
FIG. 5 shows a program edition screen displayed when the assisting program is running.

The following description explains the process carried out by the present system when the assisting program is executed by the CPU. FIG. 4 shows the flowchart of this process, and FIG. 5 shows a program edition screen displayed when the assisting program is running. FIG. 4 also shows the relationship between each step of the flowchart and the software-based functions (i.e. the candidate selection assistant, program creator, and outputter) realized by the CPU 10.

Initially, the user operates the input unit 16 to select one of the sentence input lines in the program edition screen on the display unit 14 (Step S14). As shown in FIG. 5, the program edition screen has a sentence input area with multiple lines, i.e. the sentence input lines, in which instructional sentences can be written, one sentence in one line, in the order of execution. When one of the sentence input lines is selected, the CPU 10, now functioning as the candidate selection assistant, reads out instructional sentences from the definition file 22 saved in the storage unit 20 and displays the sentences as candidates on the screen.

Figure 6:
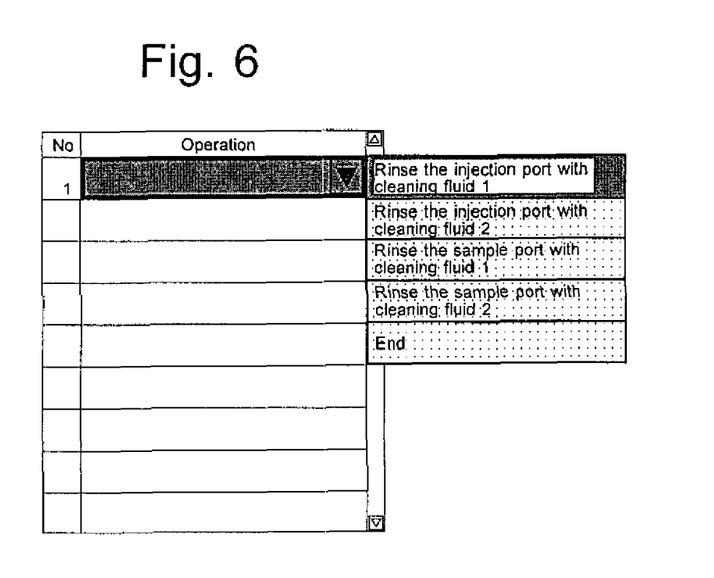
FIG. 6 shows the sentence input area of the program edition screen with one sentence input line selected.

FIG. 6 shows the sentence input area with one sentence input line selected. On the sentence input area, the user can select any sentence input line. Usually, line No. 1 is selected at the beginning. When one sentence input line selected, a plurality of candidate sentences are listed next to the selected line (Step S2). In the example of FIG. 6, there are five instructional sentences listed. Of course, it is possible to have more choices to be listed at the same time. According to necessity, the user can change the content of the candidate list by modifying the definition file 22.

Figure 7:
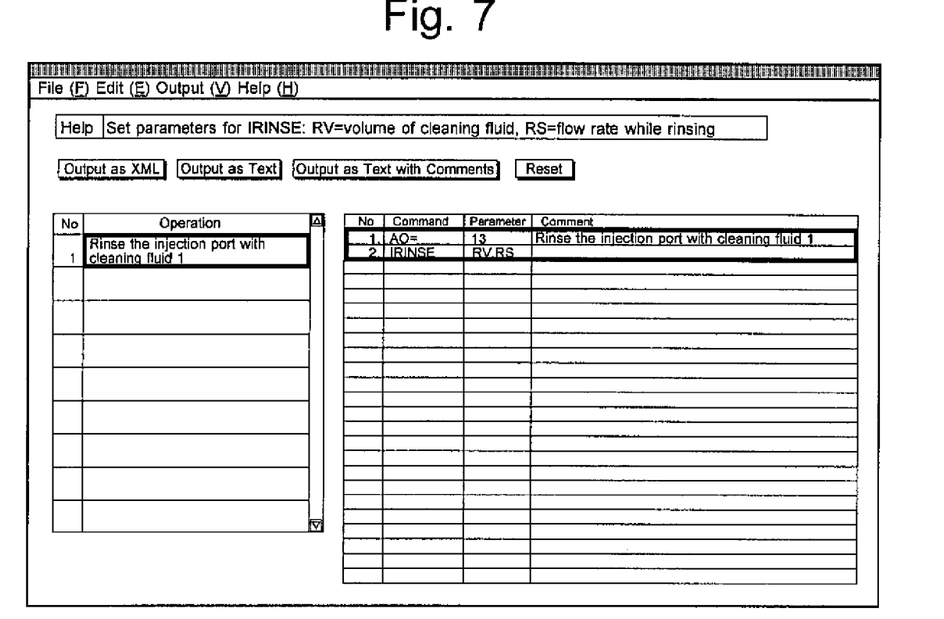
FIG. 7 shows the program edition screen with one instructional sentence selected.

Next, in Step S3, the user operates the input unit 16 to highlight one instructional sentence (for example by putting the mouse pointer on the objective instructional sentence) and select that sentence (for example by clicking the left mouse button). Upon this operation, the CPU 10 refers to the definition file 22 and reads the operational commands corresponding to the selected instructional sentence (Step S4). Now, suppose that the user has selected the instructional sentence "Rinse the injection port with the cleaning fluid 1" located at the top of the candidate list in FIG. 6. According to the definition file 22, the sentence "Rinse the injection port with the cleaning fluid 1" is associated with two operational commands of "AO=" and "IRINSE." The two commands have parameters with initial values of "15" and "RV, RS", respectively. Accordingly, these operational commands with the initial parameter values are written in the control program input area (Step S5). Since the currently selected sentence input line is the first line of the sentence input area, the two operational commands are written in the topmost lines of the control program input area, as shown in FIG. 7. It should be noted that the processes from Steps S3 through S5 correspond to the operations of the program creator (FIG. 4).

According to necessity, the user can newly set the parameter of a certain operation command in the control program input area (when an initial value of the parameter is not preset) or change an existing parameter value. In these cases, the CPU 10 functions as the parameter-setting assistant of the present invention. In response to an input of a parameter value, the CPU 10 associates the parameter value with the operational command concerned. In the example of FIG. 7, the association of the parameter is done by writing the inputted parameter value into the appropriate parameter input cell.

The user can manually input the parameter Through the keyboard included in the input unit 16. If the definition file 22 contains a list of values available for the parameter concerned, the CPU 10 can create a drop-down list or similar input component on the screen, allowing the user to select one of the available values. This method helps the user to avoid input errors.

The control program input area may further include an additional section (e.g. "Comment" column) into which the original instructional sentences can be displayed.

According to this method, even if a given instructional sentence is associated with multiple operational commands and these commands are written in multiple lines in the control program input area, it is easy to find which operational commands displayed in the control program input area correspond to that instructional sentence.

In FIG. 7, the program edition screen is provided with a "Help" information area for displaying an explanation of the meaning of each parameter and its setting method described in the definition file 22. Reading this explanation, the user can assuredly and correctly change or set the parameter value even without knowing the meaning of that parameter beforehand.

After one instructional sentence is completed as explained thus far, when the user selects the next sentence input line (usually, line No. 2), the determination result in Step S6 will be "No" and the process returns to Step S1. Then, for the second sentence input line, the process of Steps S1 through S5 is carried out to select another instructional sentence and add the operational commands corresponding to the selected sentence to the control program.

Figure 8:
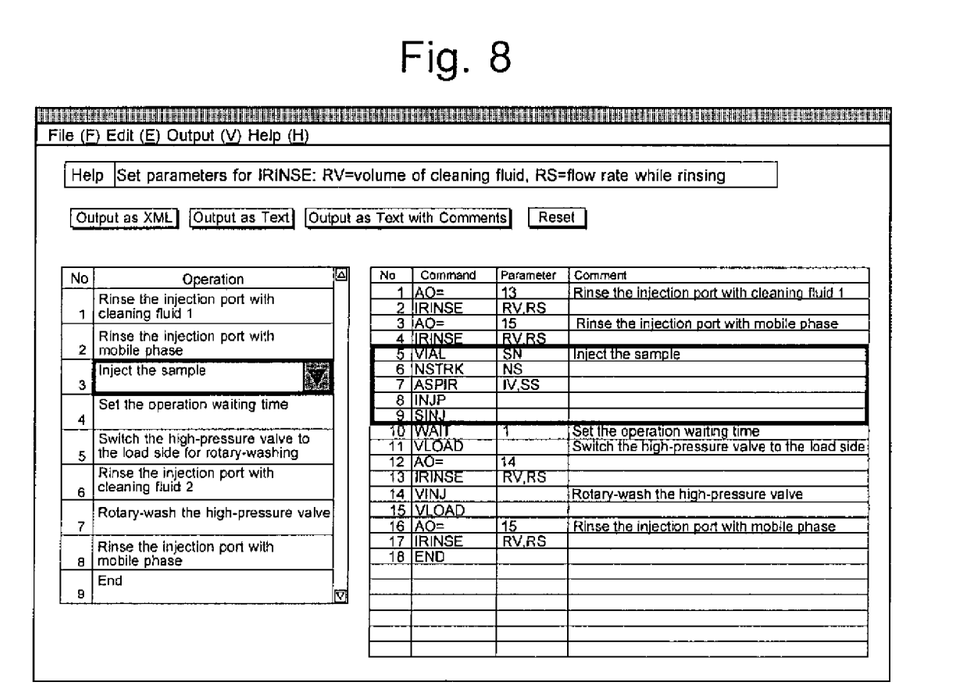
FIG. 8 shows the program edition screen with the entire control program completed.

After the process of Steps S1 through S5 has been repeated several times, the entire control program will be completed as intended by the user, for example as shown in FIG. 8. In this example, there are nine instructional sentences in line Nos. 1 through 9, one sentence in one line, and the operational commands corresponding to those instructional sentences are written in the control program input area. The last sentence in the sentence input area should be the declaration of ending the process. Accordingly, the last operational command in the last line of the control program is "END."

In the system according to this embodiment, when a new instructional sentence is additionally selected, the assisting program will create the control program so as to reorganize the operational commands in the control program input area in the right order corresponding to the new set of the operational sentences. As a result, the automatic sampler is always controlled according to the order specified by the instructional sentences.

It is also possible to change or delete an existing instructional sentence written in the sentence input area. Changing an instruction sentence can be accomplished by selecting the sentence input line in which the instructional sentence concerned is written and then choosing a new sentence from the candidate list. The sentence input area may be designed so that an instructional sentence can be "copied and pasted" or "cut and pasted" between the sentence input lines. When an instructional sentence is changed or deleted, the CPU 10 changes or deletes the corresponding operational commands in the control program input area. Also in this case, the CPU 10 (or assisting program) creates the control program so that the operational commands in the control program input area will always be in the same order as that of the operational sentences in the sentence input area.

After the control program is created, the user operates the input 16 to enter the output command. The assisting program in this embodiment supports two output file formats: XML and plain text (CSV, TSV or other text formats). Accordingly, the screen in FIG. 8 has two kinds of output buttons: "Output as XML" and "Output as Text." When the user presses one of those buttons, the CPU 10, now functioning as the outputter, creates a file in which the operational commands are written in either XML or text format. It should be noted that the choices of the output format are not always limited to the XML or text format; they can be changed according to the specifications of the automatic samplers for which the control program is to be used. The directory in which the output file is to be saved may be automatically designated by the assisting program or manually designated by the user.

The process of assisting the creation of an automatic sampler control program according to the present invention is performed as described thus far. When starting its operation, the automatic sampler reads the file in which the automatic sampler control program was written in Step S7.

The system for assisting the creation of an automatic sampler control program described thus far is a mere example of the present invention. It is of course understood that this example can be further changed or improved within the spirit and scope of the present invention, for example as follows:

[Saving the Current State of the Program]

Under certain working conditions, users of the system of the present invention may need to temporarily stop the system and later resume the task of creating or changing the control program. It is also possible that the user may want to save the state of a control program at a given point in time so that it can be later used as a template for creating various control programs. To meet such requirements, the assisting program may further include the function of creating and saving a file for recording the current state of the control program.

For example, on the program edition screen shown in FIG. 8, pressing the button labeled "Output as Text with Comments" will create a text file in which the instructional sentences written in the sentence input area and the commands with the parameters written in the control program input area are recorded.

[Hierarchically Displaying the Candidates]

If there are a large number of instructional sentences, it is possible that too many instructional sentences are displayed at one time when a sentence input line is selected in Step S1, impeding the user to quickly find an instructional sentence corresponding to the objective control operation. To solve this problem, the information in the definition file 22 may be organized in a hierarchical structure having multiple levels, with the instructional sentences located at the lowest level.

Figure 9:
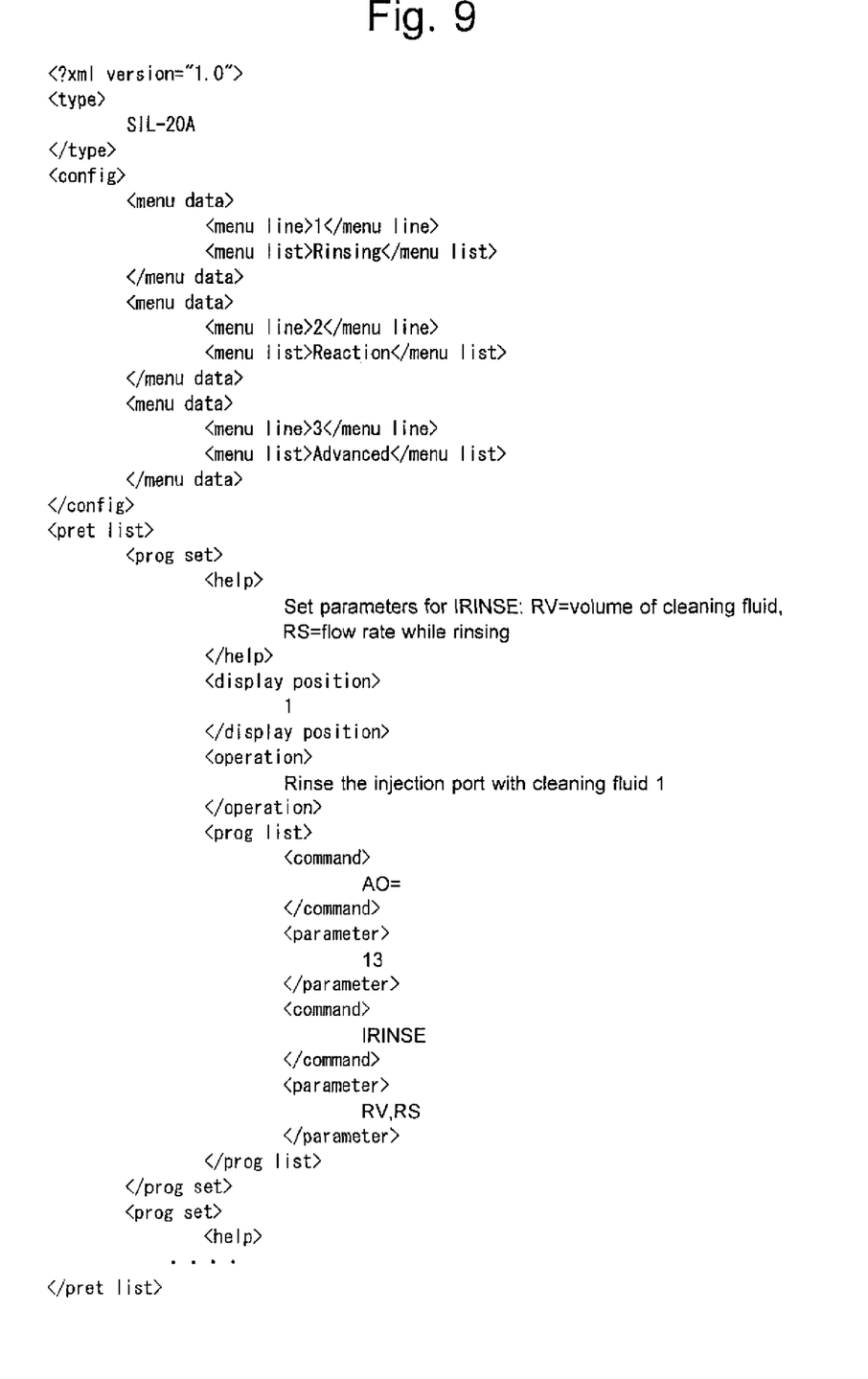
FIG. 9 shows an example of the definition file.

FIG. 9 shows an example of the definition file 22. In this example, the file is in XML format. It should be noted that FIG. 9 shows only a portion of the definition file 22 and there is only one instructional sentence defined in that portion. In fact, the definition file 22 contains the definitions of all the instructional sentences.

In the definition file 22, the three choices "Rinsing", "Reaction" and "Advanced" enclosed by the <config> tags belong to the first level of hierarchy (these choices are not instructional sentences). The instructional sentence "Rinse the injection port with the cleaning fluid 1" and the two operational commands "AO=" and "IRINSE" with their initial parameter values, which are all enclosed by the <prog set> tags, belong to the second level, which is the lowest level in the present example.

Figure 10:
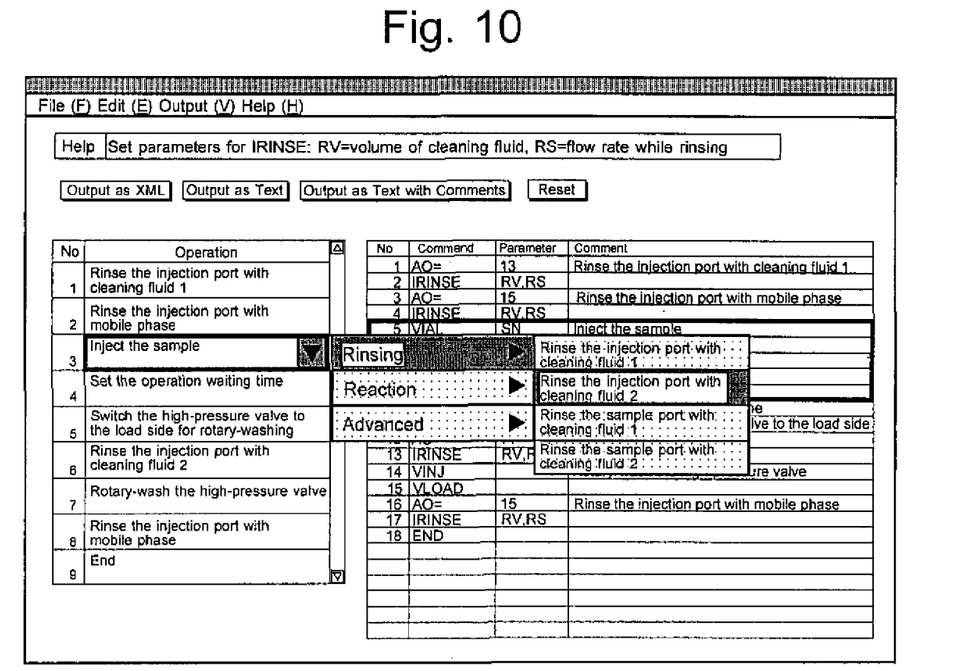
FIG. 10 shows the program edition screen with multiple candidates hierarchically displayed.

When the user has selected a sentence input line in Step S1, the CPU 10 refers to the hierarchically organized candidate information in the definition file 22 and displays the candidates in a hierarchical form. FIG. 10 shows a screen image in which four candidate sentences are displayed as defined the definition file 22 shown in FIG. 9. In FIG. 10, the user is going to change the existing sentence "Inject the sample" with a different instructional sentence. In detail, at the first level, the user has selected "Rinsing" from the three choices "Rinsing", "Reaction" and "Advanced" (for example by putting the mouse pointer on the area labeled "Rinsing" for a predetermined period of time). Then, at the second level, the four candidate sentences "Rinse the injection port with the cleaning fluid 1", "Rinse the injection port with the cleaning fluid 2", "Rinse the sample port with the cleaning fluid 1" and "Rinse the sample port with the cleaning fluid 2" are displayed.

The hierarchical displaying of the instructional choice sentences helps the user to locate the objective instructional sentence. The depth (or the number of levels) of the hierarchy, which was two in the previous example, can be changed to three or more by appropriately modifying the definition file 22.

[Linking the System With an Analyzing Apparatus]

The system of the present invention can be operated as an independent system (or program). Alternatively, it is possible to embed it into an analyzing apparatus or automatic sampler or construct it as a system (or program) that can be called and executed from the analyzing apparatus or automatic sampler. For example, the system of the present invention may be constructed so that it can be executed on the analysis program running in the controller for the analysis apparatus.

What is claimed is:

1. A computer system for assisting in a creation of an automatic sampler control program including a sequence of operational commands, wherein:

The computer system has access to a definition file in which a plurality of instructional sentences are written in a natural language and each instructional sentence is associated with one or more operational commands corresponding to that instructional sentence, and the computer system further comprises:

a central processing unit;

a memory;

an input assistant for selecting one of sentence input lines in each of which an instructional sentence can be written, for selecting an instructional sentence, for inputting a parameter, and for entering an output command;

a candidate selection assistant acting in response to a selection of one sentence input line, to read a plurality of instructional sentences from the definition file and display the read-out instructional sentences as candidates;

a program creator acting in response to a selection of one of the instructional sentences displayed as the candidates, to create the control program by reading one or more operational commands corresponding to the selected instructional sentence from the definition file and then writing the read-out operational commands in the control program in accordance with an order of the instructional sentences written in the sentence input lines;

a parameter-setting assistant acting in response to an input of a parameter of one operational command included in the control program, to associate the inputted parameter with the aforementioned one operational command; and an outputter acting in response to the output command, to output the control program in a predetermined file format.

2. The computer system according to claim 1, wherein:

the definition file contains candidate information organized in a hierarchical structure having multiple levels, with the aforementioned instructional sentences located at a lowest level; and the candidate selection assistant hierarchically displays the candidates on a basis of the candidate information.

3. The computer system according to claim 1, wherein:

the definition file specifies an initial value of each parameter of one or more specific operational commands; and for each operational command used in the control program to be created, if the initial value of each parameter of that operational command is defined, the program creator writes the operational command with the initial value of each parameter in the control program.

4. The computer system according to claim 2, wherein:

the definition file specifies an initial value of each parameter of one or more specific operational commands; and for each operational command used in the control program to be created, if the initial value of each parameter of that operational command is defined, the program creator writes the operational command with the initial value of each parameter in the control program.

5. A computer executing an assisting program for assisting in a creation of an automatic sampler control program including a sequence of operational commands, the computer having access to a definition file in which a plurality of instructional sentences are written in a natural language and each instructional sentence is associated with one or more operational commands corresponding to that instructional sentence, wherein the computer comprises:

a candidate selection assistant acting in response to a selection of one sentence input line, to read a plurality of instructional sentences from the definition file and display the read-out instructional sentences as candidates;

a program creator acting in response to a selection of one of the instructional sentences displayed as the candidates, to create the control program by reading one or more operational commands corresponding to the selected instructional sentence from the definition file and then writing the read-out operational commands in the control program in accordance with an order of the instructional sentences written in the sentence input lines;

a parameter-setting assistant acting in response to an input of a parameter of one operational command included in the control program, to associate the inputted parameter with the aforementioned one operational command; and an outputter acting in response to an output command, to output the control program in a predetermined file format.

* * * * *